United States Patent
Fachmann et al.

(10) Patent No.: US 11,029,311 B2
(45) Date of Patent: Jun. 8, 2021

(54) METHOD FOR DETERMINING A CONCENTRATION OF EPITHELIAL CELLS IN A BLOOD SAMPLE OR ASPIRATE SAMPLE

(71) Applicants: Ulrich Fachmann, Bayreuth (DE); Katharina Fachmann, Bayreuth (DE)

(72) Inventors: Ulrich Fachmann, Bayreuth (DE); Katharina Fachmann, Bayreuth (DE)

(*) Notice: Subject to any disclaimer, the term of this patent is extended or adjusted under 35 U.S.C. 154(b) by 444 days.

(21) Appl. No.: 15/751,071

(22) PCT Filed: Aug. 3, 2016

(86) PCT No.: PCT/EP2016/068541
§ 371 (c)(1),
(2) Date: Feb. 7, 2018

(87) PCT Pub. No.: WO2017/025409
PCT Pub. Date: Feb. 16, 2017

(65) Prior Publication Data
US 2018/0231549 A1    Aug. 16, 2018

(30) Foreign Application Priority Data

Aug. 7, 2015   (EP) .................................... 15180229
Sep. 10, 2015  (EP) .................................... 15184733
Sep. 24, 2015  (EP) .................................... 15186743

(51) Int. Cl.
G01N 33/53     (2006.01)
G01N 33/569    (2006.01)

(52) U.S. Cl.
CPC ............... *G01N 33/56966* (2013.01); *G01N 2333/70596* (2013.01)

(58) Field of Classification Search
None
See application file for complete search history.

(56) References Cited

U.S. PATENT DOCUMENTS

| 7,615,358 B2 | 11/2009 | Pachmann et al. | |
| 2003/0082632 A1* | 5/2003 | Shumate | G01N 33/537 435/7.1 |
| 2012/0225788 A1* | 9/2012 | Madrid | C12Q 1/533 506/9 |

FOREIGN PATENT DOCUMENTS

| WO | 2014/020169 A1 | 2/2014 |
| WO | 2014/047285 A1 | 3/2014 |

OTHER PUBLICATIONS

Qin et al., Stabilization of circulating tumor cells in blood using a collection device with a preservative reagent, Cancer Cell International, 2014, 14:23, pp. 1-6. (Year: 2014).*
Norton et al., A new Blood Collection Device Minimizes Cellular DNA Release During Sample Storage and Shippping When compared to a Standard Device, Journal of Clinical Laboratory Analysis 27, 2013, pp. 305-311. (Year: 2013).*
Pachmann et al., Standardized quantification of circulating peripheral tumor cells from lung and breast cancer, Clin Chem Lab Med, 2005, 43(6), pp. 617-627. (Year: 2005).*
Hekimian et al., "Demasking of epithelial cell adhesion molecule (EpCAM) on circulating epithelial tumor cells by Tween®20 treatment in breast cancer patients," Clin Chem Lab Med 50(4):701-708 (2012).
International Preliminary Report on Patentability, International Application Na PCT/EP2016/068541 (published as WO 2017/025409), dated Oct. 19, 2017, 13 pages (translation provided).
International Search Report and Written Opinion, International Application No. PCT/EP2016/068541 (published as WO 2017/025409), dated Sep. 3, 2016, 9 pages (translation of International Search Report provided).
Pizon et al., "Insulin-Like Growth Factor Receptor I (IGF-IR) and Vascular Endothelial Growth Factor Receptor 2 (VEGFR-2) Are Expressed on the Circulating Epithelial Tumor Cells of Breast Cancer Patients," PLOS One 8(2): (Feb. 2013), 6 pages.
Response to International Search Report and Demand, International Application No. PCT/EP2016/068541 (published as Wo 2017/025409), dated Mar. 7, 2017, 10 pages.
Response to International Search Report, International Application No. PCT/EP2016/068541 (published as WO 2017/025409), dated Sep. 7, 2017, 13 pages (partial translation provided).
Zhao et al., "Comparison and development of two different solid phase chemiluminescence ELISA for the determination of albumin in urine," Analytica Chimica Acta 541:199-207 (2005).

* cited by examiner

*Primary Examiner* — Gary Counts
(74) *Attorney, Agent, or Firm* — Prismatic Law Group, PLLC

(57) ABSTRACT

A method for determining a concentration of epithelial cells in a blood sample or aspirate sample originating from a human being or mammal and mixed with anti-clotting agent. Here, following the addition of antibodies, antibody fragments, or antibody mimetica, which are each aimed against an antigen that is specific to epithelial cells, the sample is incubated until a decreasing binding rate of the binding of the antibodies, antibody fragments, or antibody mimetica to the cells is achieved. Only then is the number of marked cells and the original concentration of the cells in the blood sample or aspirate sample determined.

19 Claims, No Drawings

METHOD FOR DETERMINING A CONCENTRATION OF EPITHELIAL CELLS IN A BLOOD SAMPLE OR ASPIRATE SAMPLE

This application is a 371 national phase of International Application No. PCT/EP2016/068541 filed Aug. 3, 2016, which claims priority to European Application No. 15186743.9 filed Sep. 24, 2015, European Application No. 15184733.2 filed Sep. 10, 2015, and European Application No. 15180229.5 filed Aug. 7, 2015, the contents of each of which applications is incorporated herein by reference.

The invention relates to a method for determining a concentration of epithelial cells in a blood sample or aspirate sample which originates from a human or mammal and has been admixed with an anticoagulant. The aspirate sample can be a sample of a bone marrow aspirate, of a pleural aspirate or of a peritoneal aspirate.

Such a method is known from U.S. Pat. No. 7,615,358 B2. In said method, epithelial tumor cells present in a body fluid are labeled by addition of antibodies or antibody fragments, the antibodies or antibody fragments being directed against the human epithelial antigen which is recognized by the monoclonal antibody HEA 125. The sample is subsequently applied to a support and incubated in order to allow the tumor cells to adhere to the support. In this connection, the surface of the support can be coated with an agent which supports nonspecific cell binding, such as, for example, poly-L-lysine. The adhesion of the cells usually takes 10 to 15 minutes. Thereafter, viable cells of the adhering epithelial tumor cells are identified via their morphology and quantified and the concentration of viable epithelial tumor cells in the body fluid is calculated. This involves analyzing the morphology of the adhering epithelial tumor cells by means of laser scanning cytometry, wherein living tumor cells are detected through their exclusive surface staining and dead cells are eliminated on the basis of their intracellular staining.

WO 2014/047285 A1 discloses a method for detecting and/or treating a subgroup of prostate cancer patients who may benefit from taxane treatment. In said method, it is determined whether an androgen receptor splice variant is present in a sample collected from the patients. For this purpose, circulating tumor cells can be captured from the sample and tested for the presence of one of the specific splice variants. Capture can be effected by means of immobilized antibodies. Testing comprises contacting the sample with an antibody directed against the splice variant and detecting binding of the antibody to the splice variant.

Pizon, M. et al., PLOS ONE, February 2013, volume 8, issue 2, e56836, pages 1 to 6, disclose a method for determining IGF receptor I and VEGF receptor 2 on circulating epithelial tumor cells in blood samples from breast cancer patients. In said method, the blood samples treated with EDTA as anticoagulant were processed within 48 hours after the collection thereof. In addition, the erythrocytes in the blood sample were lysed. The remaining cells were incubated overnight at 4° C. with PE-labeled mouse monoclonal antibodies directed against VEGF receptor 2 as well as FITC-conjugated mouse antibodies directed against EpCAM or PE-labeled mouse monoclonal antibodies directed against IGF receptor I as well as FITC-conjugated mouse antibodies directed against EpCAM. A defined volume of the resulting cell suspensions was transferred into wells of ELISA plates and measured using a laser scanning cytometer.

Hekimian, K. et al., Clin. Chem. Lab. Med. 2012; 50(4), pages 701-708, disclose TWEEN® 20 (polyoxyethylene (20) sorbitan monolaureate) treatment to demask epithelial cell adhesion molecules (EpCAM) on epithelial tumor cells circulating in breast cancer patients. The publication speculates that EpCAM is masked by glycoproteins or membrane lipoproteins, meaning that antibody binding is prevented as a result. In one experiment, 1 ml at a time of anticoagulated peripheral blood was incubated for 5 min with 20 µl of TWEEN® 20 or without the detergent, in each case on the day of collection, on the first day after collection and on the second day after collection. Thereafter, the erythrocytes present therein were lysed with an erythrocyte lysis buffer. Epithelial cells were then detected with an antibody directed against EpCAM. It was found here that, with TWEEN® 20 treatment on the day of collection, on day 1 after collection and on day 2 after collection, it was possible to detect a cell number that was equally high within tolerance. In the absence of TWEEN® 20, it was not possible on the day of collection to detect any cells, it was possible on the first day to detect somewhat fewer cells than under TWEEN® 20 treatment, and it was possible on the second day to detect just as many cells as under TWEEN® 20 treatment. This shows that storage of the blood samples before the incubation with the antibodies also increases the accessibility of EpCAM on the cells to the antibodies.

It is an object of the present invention to provide an alternative method for determining a concentration of epithelial tumor cells in a blood sample or aspirate sample which originates from a human or mammal and has been admixed with an anticoagulant.

The invention provides a method for determining a concentration of epithelial cells in a blood sample or aspirate sample which originates from a human or mammal and has been admixed with an anticoagulant. In said method, after addition of antibodies, antibody fragments or antibody mimetics which are each directed against an antigen specific for epithelial cells, the sample is stored until the increase in the number of cell-bound antibodies, antibody fragments or antibody mimetics as a function of time slows down, i.e., until the binding rate decreases or until a binding curve obtained by plotting binding against time starts to flatten out and to pass into the saturation zone. Only then is the number of labeled cells and, therefrom, the original concentration of said cells in the blood sample or aspirate sample determined. Specifically, it was found that, astonishingly, the attainment of the start of the flattening-out of the saturation curve takes very much longer than would be expected for a given number of binding partners. It is suspected that many of the antigens specific for epithelial cells are initially present in a masked state and only become accessible to binding of the antibodies, antibody fragments or antibody mimetics over time. Only then is it possible to reliably determine the cell number.

Specifically, the method according to the invention for determining a concentration of epithelial cells in a blood sample or aspirate sample which originates from a human or mammal and has been admixed with an anticoagulant comprises the following steps:

a) lysing the erythrocytes present in the blood sample or aspirate sample by addition of a buffer which brings about a lysis of the erythrocytes, segregating cells which are not lysed in the course of this, and suspending the segregated cells in a buffer, b) adding the antibodies, antibody fragments or antibody mimetics which each bear at least one label and which are each directed against the epithelial cell adhesion molecule (EpCAM) and/or at least one other antigen specific for epithelial cells to a cell suspension obtained in step a) or to a subquantity of said cell suspension, which subquantity has been obtained by segregation, mixing the antibodies, antibody fragments or antibody mimetics and the cell suspension or the subquantity, and incubating a mixture obtained as a result for at least a time which is required for the attainment of a decreasing binding rate of binding of the antibodies, antibody fragments or antibody mimetics to the cells, wherein the incubation is done for at least 12 hours, c) determining the number of cells labeled by binding of the antibodies, antibody fragments or antibody mimetics, in the mixture obtained in step b), and d) calculating the concentration of the labeled cells, the number of which has been determined in step c), in the blood sample or aspirate sample.

The entire method is carried out outside the human body and outside the animal body. The mixing of the antibodies, antibody fragments or antibody mimetics and the subquantity according to step b) can be done immediately after the addition of the antibodies, antibody fragments or antibody mimetics to the subquantity. The incubation according to step b) can be done at a predefined temperature, for example 0 to 20° C., especially 2 to 15° C.

When calculating the concentration of the labeled cells, the number of which has been determined in step c), in the blood sample or aspirate sample according to step d), any previously performed dilution and/or concentration of the cells with respect to the blood sample or aspirate sample must be taken into account.

Normally, no epithelial cells are found in the circulating blood. However, it has become apparent that, in the blood of patients with a malignant epithelial tumor, such as a lung tumor, breast tumor, intestinal tumor or prostate tumor for example, circulating epithelial tumor cells are found in the blood. Furthermore, it has become apparent that, in the blood of patients with chronic inflammatory diseases of an epithelial tissue, such as rheumatoid arthritis, asthma, COPD, Crohn's disease or ulcerative colitis for example, epithelial cells of said tissue can be found in the peripheral blood. Furthermore, epithelial cells find their way into the peripheral blood as a result of events which damage epithelial tissue, such as an operation or a contusion for example. Therefore, it is useful for the purposes of diagnosing an epithelial tumor disease or a chronic inflammatory disease of an epithelial tissue, for the monitoring of a disease course or healing process, and for medical check-ups or mass screenings, when the concentration of epithelial cells in a blood sample or aspirate sample which originates from a human or mammal can be determined as accurately as possible. In this connection, the cells can be cells of an epithelial tumor, epithelial cells from an inflamed tissue, or other epithelial cells which have entered into the bloodstream as a result of an event which damages epithelial tissue.

The anticoagulant can, for example, be ethylenediaminetetraacetate (EDTA), citrate or heparin.

The antibody fragments can, for example, be Fab', F(ab')$_2$ or Fab. However, they can also be recombinant antibody fragments, for example scFv, di-scFv, sdAb (single-domain antibody), or chemically bonded antibody fragments such as F(ab')$_2$. Antibody mimetics are compounds which are, like antibodies, capable of binding antigens, but without being antibodies or antibody fragments themselves. In most cases, they are usually artificial peptides, proteins or lectins.

The determination of the quantity of bound antibodies, antibody fragments or antibody mimetics according to step c) is done as a function of time starting from the mixing according to step b). How a binding rate is determined is known to a person skilled in the art in the field of studying the binding of antibodies, antibody fragments or antibody mimetics to substrates.

The inventors of the present invention have discovered that the binding of the labeled antibodies, antibody fragments or antibody mimetics to an epithelial cell-specific antigen on the surface of the circulating epithelial cells does not, as is to be expected, reach saturation within a period of a few minutes after the addition and mixing thereof, but that instead saturation is achieved only after several hours. Since this cannot solely be based on the antigen-antibody reaction, it is assumed that there is an increasing accessibility of previously masked epitopes. The accessibility is already increased by storage prior to incubation with the antibodies, as is known from Hekimian, K. et al. However, it is increased again by a prolonged incubation in the presence of the antibodies, antibody fragments or antibody mimetics. The reason therefor might be that, as a result of the binding thereof, a demasking of the antigens is achieved. Such an effect is completely surprising to a person skilled in the art.

The following further steps can be carried out between steps a) and b):

a1) segregating at least one subquantity or a further subquantity of the cell suspension obtained in step a), a2) adding the antibodies, antibody fragments or antibody mimetics which each bear at least one label and which are each directed against the epithelial cell adhesion molecule (EpCAM) and/or at least one other antigen specific for epithelial cells to the further subquantity in such a quantity that the concentration thereof in the further subquantity is identical to the concentration of the antibodies, antibody fragments or antibody mimetics in the cell suspension or the subquantity according to step b), mixing the antibodies, antibody fragments or antibody mimetics and the further subquantity, and incubating a mixture obtained as a result at a/the predefined temperature and a3) continuously or repeatedly determining a quantity of antibodies, antibody fragments or antibody mimetics which have bound to cells present in the further subquantity as a function of time starting from the mixing according to step a2), ascertaining a binding rate therefrom, and determining a time which is required for the attainment of a decreasing binding rate of the binding of the antibodies, antibody fragments or antibody mimetics to said cells, wherein the incubation in step b) is done at the predefined temperature, wherein the time according to step b) is selected such that it is at least as long as the time determined in step a3).

The quantity of antibodies, antibody fragments or antibody mimetics that is to be determined in step a3) can be a relative quantity or an absolute quantity. A relative quantity is sufficient for the determination of a decreasing binding rate. When steps a) to c) or a) to d) are carried out repeatedly under identical conditions, it is sufficient when steps a1) to a3) for determining the time according to step a3) are carried out once only and the time according to step b) is then selected in each case such that it is at least as long as the time determined once only in step a3).

As is customary in binding experiments, the antibodies, antibody fragments or antibody mimetics in steps a2) and b) are each added in such a quantity that the concentration thereof in the cell suspension, the subquantity or the further subquantity exceeds by far, but at least by a factor of 2, the likely concentration of EpCAM or other antigen specific for epithelial cells.

In steps b) and a2), it is possible after addition of the antibodies, antibody fragments or antibody mimetics and an incubation for 5 to 60 minutes, for example after 15 minutes, or between steps b) and c) or a2) and a3) to carry out a dilution of the suspension, for example with PBS, in order to obtain better measurement results in the determination according to steps c) and a3), for example because a background signal resulting from the unbound antibodies, antibody fragments or antibody mimetics is reduced.

As a result of the determination according to step a3), the incubation time of the cells with the antibodies, antibody fragments or antibody mimetics that is required for the reliable determination of a concentration of epithelial cells is determined. Said time can be between 8 and 25 hours. However, if a comparatively high temperature is selected, a decreasing binding rate can also be attained even earlier, for example after 6 to 8 hours. Vice versa, in the case of a comparatively low temperature, i.e., a temperature of from 0 to 8° C., especially 2 to 8° C., the attainment of a decreasing binding rate may also require more than 25 hours and may, for example, take place only after 25 to 30 hours.

The predefined temperature can be a temperature in the range from 0 to 30° C., especially 0 to 20° C., especially 2 to 15° C., especially 8 to 15° C.

The incubation according to step b) can, for example, be done for at least 13 hours, at least 14 hours, at least 15 hours, at least 16 hours, at least 17 hours, at least 18 hours, at least 19 hours, at least 20 hours, at least 21 hours, at least 22 hours, at least 23 hours, at least 24 hours, at least 25 hours, at least 26 hours, at least 27 hours, at least 28 hours, at least 29 hours, or at least 30 hours.

The label can be a fluorescent label by means of a fluorochrome, such as fluorescein isothiocyanate (FITC) or phycoerythrin (PE) for example, a color label by means of a chromophore, or an indirectly detectable label by means of biotin, avidin, streptavidin or some other affinity tag, epitope tag or protein tag. Direct labeling of the antibody has the advantage, compared with indirect labeling, for example by means of a secondary antibody, that a wash step in which a portion of the epithelial cells usually goes missing can be omitted.

The determination of the quantity of bound antibodies, antibody fragments or antibody mimetics according to step a3) and/or the determination of the number of cells labeled by binding of the antibodies, antibody fragments or antibody mimetics according to step c) can be done by means of laser scanning cytometry, fluorescence microscopy, more particularly quantitative fluorescence microscopy, or light microscopy, more particularly quantitative light microscopy. If the determination of the quantity of bound antibodies, antibody fragments or antibody mimetics and/or the determination of the number of labeled cells is done by means of fluorescence microscopy or light microscopy, an image recognition software can be used to identify the cells. Said software can distinguish labeled cells from labeled cell debris or other nonspecifically labeled structures.

If the label is a fluorescent label, what can be dynamically determined in the laser scanning cytometry or the fluorescence microscopy for each of the cells are a total fluorescence per cell and a background fluorescence for said cell, such that it is possible to obtain equivalent fluorescence values for the cells, in each case as the difference between the total fluorescence ascertained for the particular cell and the background fluorescence ascertained for said cell. When dynamically determining the background fluorescence, what is measured in each case when measuring the total fluorescence of a cell is, at the time of said measurement, also the fluorescence of the background in the region of said cell, i.e., at a distance of up to about half a cell diameter from the cell membrane of said cell. This makes it possible to increase the accuracy of the particular measurement and the validity of the measurement results.

The segregation of the unlysed cells according to step a) can be done by centrifugation, mere sedimentation or filtration. The suspension of the segregated cells in a buffer according to step a) is done immediately after the segregation, i.e., such that the cells do not dry and are not damaged by the drying after the segregation. The buffer can be PBS, i.e., a phosphate-buffered saline solution.

In one embodiment of the method, a blocking reagent for the blocking of nonspecific binding sites and/or of Fc receptors is added to the cell suspension, the subquantity or the further subquantity of the cell suspension and mixed and incubated with the cell suspension, the subquantity or the further subquantity of the cell suspension, in each case before the addition of antibodies, antibody fragments or antibody mimetics which each bear at least one label according to steps b) and a2). In this connection, the incubation can, for example, be done at 8° C. for about 15 minutes.

In one embodiment of the method, in none of the steps is a detergent used and/or in none of the steps are the cells fixed. As a result, it is possible to avoid damage to the epithelial cells and thus an impact on the measurement results. This is especially significant when it is intended that a concentration of cells with intact cell membrane or even a concentration of living epithelial cells be determined in the method.

All the steps of the method or at least steps b) and c) or at least steps b), a2), a3) and c) can be carried out in an automated manner by a machine designed for this purpose. As a result, it is possible to achieve an objectivization and improvement in the reproducibility of the measurement results.

In one embodiment of the method, two or more subquantities are segregated in step a1), wherein, in step a2), a different quantity of the antibodies, antibody fragments or antibody mimetics is added in each case to each of the subquantities and mixed, in particular immediately, with the respective subquantities, wherein, in step a3), the time required for the attainment of the decreasing binding rate is determined for each of the subquantities, wherein that quantity of the antibodies, antibody fragments or antibody mimetics in which the decreasing binding rate is attained within a desired time is then selected for the performance of step b).

The other antigen specific for epithelial cells can, for example, be selected from the following group: androgen receptor, epithelial growth factor receptor (EGF receptor), estrogen receptor, progesterone receptor, prostate-specific antigen (PSA), prostate-specific membrane antigen (PSMA), programmed death ligand 1 (PDL-1), melan A, B7-H3, vascular endothelial growth factor receptor (VEGF receptor), Ki67, insulin-like growth factor receptor (IGF receptor) and Her2neu.

The blood sample or the aspirate sample can be stored at a temperature between 0 and 40° C., especially at a temperature between 15 and 25° C., for at least 14 hours, especially at least 16 hours, especially at least 18 hours, especially at least 20 hours, especially at least 22 hours, especially at least 24 hours, before the erythrocytes are lysed. As a result, it is possible to achieve a further improvement in the accessibility of the antigens specific for epithelial cells.

The invention will be more particularly elucidated below on the basis of an exemplary embodiment.

1 ml of blood anticoagulated with EDTA is left to stand at room temperature for 24 hours. Thereafter, the sample is topped up to 15 ml with erythrocyte lysis buffer (155 mM $NH_4Cl$, 10 mM $KHCO_3$, 1 mM $Na_2$ EDTA) and stored at 8° C. for 15 minutes. Thereafter, the sample is centrifuged at 780 g for 7 minutes. The supernatant is completely discarded. The pellet is resuspended in 500 µl of PBS-EDTA (137 mM NaCl, 2.8 mM KCl, 8.1 mM $NaHPO_4$, 1.47 mM $KH_2PO_4$, 2 mM EDTA, pH 7.4).

From the sample, 50 µl are added to a reaction tube and admixed with 15 µl of FcR blocking reagent (Miltenyi Biotec GmbH) and incubated at 8° C. for 15 minutes. Thereafter, 5 µl of a monoclonal antibody directed against EpCAM (HEA-125, Miltenyi Biotec GmbH) are added and mixed with the suspension. This is followed by a 15-minute incubation at 8° C. under protection from light. Thereafter, 430 µl of PBS-EDTA are added and mixed with the suspension. The resulting suspension is incubated in the dark at 8° C. After renewed mixing, 100 µl at a time are taken off therefrom after different times and measured using an iCys laser scanning microscope (CompuCyte, Beckman Coulter GmbH). The measurement can also be done using a different microscope suitable for fluorescence capture. From the measured binding at different times, it is possible to determine the time, starting from the mixing with the antibody, which is required for the attainment of a decreasing binding rate.

Thereafter, another 50 µl of the cell pellet resuspended in PBS-EDTA are admixed with 15 µl of FcR blocking reagent and, after mixing, incubated at 8° C. for 15 minutes. Thereafter, 5 µl of the abovementioned antibody directed against EpCAM are added and mixed with the cell suspension. After 15 minutes of incubation at 8° C. under protection from light, 430 µl of PBS-EDTA are added and mixed with the suspension. Thereafter, the suspension is incubated in the dark at 8° C. for the time required for the attainment of a decreasing binding rate, for example 14 or 16 hours. After a renewed thorough mixing of the suspension, 100 µl thereof are taken off and examined under the laser scanning microscope or another microscope suitable for fluorescence capture. In said examination, the number of cells labeled by binding of the antibodies is determined and, from this, the concentration of said cells in the original blood sample.

The invention claimed is:

1. A method for determining a concentration of epithelial cells in a blood sample or aspirate sample which originates from a human or mammal and has been admixed with an anticoagulant, comprising the following steps:
   a) lysing the erythrocytes present in the blood sample or aspirate sample by addition of a buffer which brings about a lysis of the erythrocytes, segregating cells which are not lysed in the course of this, and suspending the segregated cells in a buffer, wherein the blood sample or the aspirate sample is stored at a temperature between 0 and 40° C. for at least 24 hours before the erythrocytes are lysed,
   b) adding antibodies, antibody fragments or antibody mimetics which each bear at least one label and which are each directed against the epithelial cell adhesion molecule (EpCAM) and/or at least one other antigen specific for epithelial cells to a cell suspension obtained in step a) or to a subquantity of said cell suspension, which subquantity has been obtained by segregation, mixing the antibodies, antibody fragments or antibody mimetics and the cell suspension or the subquantity, and incubating a mixture obtained as a result for at least a time which is required for the attainment of a decreasing binding rate of binding of the antibodies, antibody fragments or antibody mimetics to the cells, wherein the incubation is done for at least 12 hours,
   c) determining the number of cells labeled by binding of the antibodies, antibody fragments or antibody mimetics, in the mixture obtained in step b), and
   d) calculating the concentration of the labeled cells, the number of which has been determined in step c), in the blood sample or aspirate sample.

2. The method as claimed in claim 1, wherein the following further steps are carried out between steps a) and b):
   a1) segregating at least one subquantity or a further subquantity of the cell suspension obtained in step a),
   a2) adding the antibodies, antibody fragments or antibody mimetics which each bear at least one label and which are each directed against the epithelial cell adhesion molecule (EpCAM) and/or at least one other antigen specific for epithelial cells to the further subquantity in such a quantity that the concentration thereof in the further subquantity is identical to the concentration of the antibodies, antibody fragments or antibody mimetics in the cell suspension or the subquantity according to step b), mixing the antibodies, antibody fragments or antibody mimetics and the further subquantity, and incubating a mixture obtained as a result at a predefined temperature and
   a3) continuously or repeatedly determining a quantity of said antibodies, said antibody fragments or said antibody mimetics which have bound to cells present in the further subquantity as a function of time starting from the mixing according to step a2), ascertaining a binding rate therefrom, and determining a time which is required for the attainment of a decreasing binding rate of the binding of said antibodies, said antibody fragments or said antibody mimetics to said cells,
   wherein the incubation in step b) is done at the predefined temperature, wherein the time according to step b) is selected such that it is at least as long as the time determined in step a3).

3. The method as claimed in claim 1, wherein the incubation according to step b) is done at a predefined temperature and/or wherein the predefined temperature is a temperature in the range from 0 to 30° C.

4. The method as claimed in claim 1, wherein the incubation according to step b) is done for at least 13 hours, at least 14 hours, at least 15 hours, at least 16 hours, at least 17 hours, at least 18 hours, at least 19 hours, at least 20 hours, at least 21 hours, at least 22 hours, at least 23 hours, at least 24 hours, at least 25 hours, at least 26 hours, at least 27 hours, at least 28 hours, at least 29 hours, or at least 30 hours.

5. The method as claimed in claim 1, wherein the label is a fluorescent label by means of a fluorochrome, a color label by means of a chromophore, or an indirectly detectable label by means of an affinity tag, epitope tag or protein tag.

6. The method as claimed in claim 1, wherein the determination of the number of cells labeled by binding of the antibodies, antibody fragments or antibody mimetics according to step c) is done by means of laser scanning cytometry, fluorescence microscopy or light microscopy.

7. The method as claimed in claim 6, wherein the determination of the quantity of bound antibodies, antibody fragments or antibody mimetics and/or the determination of the number of labeled cells is done by means of fluorescence microscopy or light microscopy and an image recognition software is used to identify the cells.

8. The method as claimed in claim 6, wherein the label is a fluorescent label and wherein determined, at different times, in the laser scanning cytometry or the fluorescence microscopy for each of the cells are a total fluorescence per cell and a background fluorescence for said cell, such that equivalent fluorescence values are obtained for the cells, in each case as the difference between the total fluorescence ascertained for the particular cell and the background fluorescence ascertained for said cell.

9. The method as claimed in claim 1, wherein the segregation according to step a) is done by centrifugation, sedimentation or filtration.

10. The method as claimed in claim 1, wherein a blocking reagent for the blocking of nonspecific binding sites and/or of Fc receptors is added to the cell suspension or the subquantity of the cell suspension and mixed and incubated with the cell suspension or the subquantity of the cell suspension, in each case before the addition of antibodies, antibody fragments or antibody mimetics which each bear at least one label according to steps b).

11. The method as claimed in claim 1, wherein in none of the steps is a detergent used and/or in none of the steps are the cells fixed.

12. The method as claimed in claim 1, wherein all the steps of the method or at least steps b) and c) are carried out automatically by a machine.

13. The method as claimed in claim 2, wherein two or more subquantities are segregated in step a1), wherein, in step a2), a different quantity of the antibodies, antibody fragments or antibody mimetics is added in each case to each of the subquantities and mixed with the respective subquantity, wherein, in step a3), the time required for the attainment of the decreasing binding rate is determined for each of the subquantities, wherein that quantity of the antibodies, antibody fragments or antibody mimetics in which the decreasing binding rate is attained within a desired time is then selected for the performance of step b).

14. The method as claimed in claim 1, wherein the other antigen specific for epithelial cells is selected from the group consisting of: androgen receptor, epithelial growth factor receptor (EGF receptor), estrogen receptor, progesterone receptor, prostate-specific antigen (PSA), prostate-specific membrane antigen (PSMA), programmed death ligand 1 (PDL-1), melan A, B7-H3, vascular endothelial growth factor receptor (VEGF receptor), Ki67, insulin-like growth factor receptor (IGF receptor) and Her2neu.

15. The method as claimed in claim 7, wherein the label is a fluorescent label and wherein determined, at different times, in the laser scanning cytometry or the fluorescence microscopy for each of the cells are a total fluorescence per cell and a background fluorescence for said cell, such that equivalent fluorescence values are obtained for the cells, in each case as the difference between the total fluorescence ascertained for the particular cell and the background fluorescence ascertained for said cell.

16. The method as claimed in claim 5, wherein the indirectly detectable label is by means of biotin, avidin, or streptavidin.

17. The method as claimed in claim 2, wherein the determination of the quantity of bound antibodies, antibody fragments or antibody mimetics according to step a3) is done by means of laser scanning cytometry, fluorescence microscopy or light microscopy.

18. The method as claimed in claim 2, wherein a blocking reagent for the blocking of nonspecific binding sites and/or of Fc receptors is added to the cell suspension, the subquantity or the further subquantity of the cell suspension and mixed and incubated with the cell suspension, the subquantity or the further subquantity of the cell suspension, in each case before the addition of antibodies, antibody fragments or antibody mimetics which each bear at least one label according to steps b) and a2).

19. The method as claimed in claim 2, wherein all the steps of the method or at least steps b), a2), a3) and c) are carried out automatically by a machine.

* * * * *

UNITED STATES PATENT AND TRADEMARK OFFICE
CERTIFICATE OF CORRECTION

PATENT NO. : 11,029,311 B2
APPLICATION NO. : 15/751071
DATED : June 8, 2021
INVENTOR(S) : Ulrich Pachmann and Katharina Pachmann Page 1 of 1

It is certified that error appears in the above-identified patent and that said Letters Patent is hereby corrected as shown below:

On the Title Page

Under item (12), please replace "Fachmann et al." with "Pachmann et al."

Under "Applicants:" item (71), in both instances please replace "Fachmann" with "Pachmann"

Under "Inventors:" item (72), in both instances please replace "Fachmann" with "Pachmann"

Signed and Sealed this
Seventh Day of December, 2021

Drew Hirshfeld
*Performing the Functions and Duties of the*
*Under Secretary of Commerce for Intellectual Property and*
*Director of the United States Patent and Trademark Office*